United States Patent [19]
O'Brien

[11] Patent Number: 5,320,107
[45] Date of Patent: Jun. 14, 1994

[54] SPIROMETER WITH ZONE GRAPH

[76] Inventor: Kevin P. O'Brien, 41 Vermont Ave., Cincinnati, Ohio 45215

[21] Appl. No.: 996,611

[22] Filed: Dec. 24, 1992

[51] Int. Cl.⁵ .............................................. A61B 5/087
[52] U.S. Cl. ...................................... 128/725; 128/726
[58] Field of Search .......................... 128/716, 725-730

[56] References Cited

U.S. PATENT DOCUMENTS

| | | | |
|---|---|---|---|
| 3,367,324 | 2/1968 | De Bono | 128/727 |
| 3,862,628 | 1/1975 | Williams. | |
| 4,041,935 | 8/1977 | Garbe. | |
| 4,158,360 | 6/1979 | Adams. | |
| 4,284,083 | 8/1981 | Lester | 128/725 |
| 4,391,283 | 7/1983 | Sharpless et al. | 128/727 X |
| 4,944,306 | 7/1990 | Alvino. | |

Primary Examiner—Angela D. Sykes
Attorney, Agent, or Firm—Charles R. Wilson

[57] ABSTRACT

A spirometer for in-home use by an individual with a respiratory disorder such as asthma measures the individual's current lung expiratory peak flow rate and provides a means to compare the current peak flow rate to a historical peak flow rate. The spirometer comprises an air flow channel having a terminus to receive air blown into it by the individual, a flow rate measuring chamber in communication with the air flow channel, and an adjustable zone graph in operable association with the flow rate measuring chamber. The zone graph has a series of zones to indicate the individuals current peak rate and compare it to the individual's previously determined peak flow rate as measured at a fully healthy period of time. A visual comparison of the peak flow rates can alert the individual to an on-coming asthma attack prior to the individual suffering from any asthma symptoms.

14 Claims, 3 Drawing Sheets

SPIROMETER WITH ZONE GRAPH

This relates to a spirometer. More particularly, the invention relates to a spirometer for in-home use by an individual wherein the spirometer has the capability to compare a current lung expiratory peak flow rate with a historical peak flow rate.

Respiratory disorders of various natures are experienced by many people. Asthma in particular is a respiratory disorder which is well known because of the large number of people who suffer from it. Asthma involves a narrowing of the individual's bronchial tubes with consequent breathing difficulties. A mild asthmatic condition causes discomfort and affects the individual's lifestyle. The individual will suffer shortness of breath and wheezing. More severe asthmatic attacks can be fatal.

Medications are known which are very effective in providing relief to the asthma sufferer. For example, bronchodilators are quite commonly prescribed for dilating the bronchial tubes to increase the flow of air to the lungs. The relief provided by the medication is almost immediate. It can be self administered by the individual provided the asthma attack is mild. A visit to the doctor or even admission to a hospital on an emergency basis is necessary in more severe attacks.

Periodic self-medication can be used to prevent an asthma attack from ever occurring in certain instances and with some people. However, for many people the type of medication or the proper dosage level can be difficult to determine in advance. While certain asthma causing conditions such as seasonably high pollen counts are determinable and the asthma sufferer will take steps to avoid the cause or at least begin taking medication to prevent an asthma attack, other asthma causing conditions are not so easily predicted.

Use of a hand-held spirometer commonly known as a peak flow meter is becoming more prevalent with people who have suffered from asthma. The peak flow meter is able to measure an individual's maximum lung exhalation rate. This gives a measure of that person's current lung function. The instrument is inexpensive and easy to use. The individual simply blows into the instrument and a peak flow rate for that individual is determined. Periodic use of the peak flow meter will tell the individual when his lung expiratory rate is decreasing. Often, the decreasing flow rate will precede any of the common asthma symptoms such as shortness of breath, coughing and wheezing. This will allow the individual to begin or perhaps increase his medication or possibly to contact his physician for further instructions. Without such an objective measurement, asthma patients typically underestimate the severity of their condition.

A recognized drawback with known peak flow meters is that any reading taken from one is not meaningful unless it relates to that individual's past performance. There is no absolute number or simple chart that can accurately predict a standard for the peak flow rate of an individual patient. Peak flow rates gradually increase into the third decade of life, then gradually decline with further aging. Besides age, other factors which affect a predicted peak flow rate include height, weight, sex, race, and strength. There are too many variables to allow an accurate prediction of peak flow rate for any one individual. Therefore, physicians rely on a standard set by each individual patient to which future peak flow rate measurements are compared. This concept employs recognition of a "personal best" peak flow rate. This becomes established in the first few weeks of daily spirometer use. If this personal best record is considered to be this patient's "100% level" then therapy can be guided when peak flow rates are converted to percentages relative to this individual standard. Since options for connecting therapy to this result are limited, most physicians find it useful to merely have the peak flow rate identify a "zone" in which the patient is in. A typical zone in popular use is GREEN=80 to 100% of personal best=GOOD; YELLOW=65 to 80% of personal best=CAUTION; ORANGE=50 to 65% of personal best=WARNING; and RED=0 to 50% of personal best=DANGER! Such a qualitative system has been shown to be adequate in guiding therapy.

Despite the apparent simplicity of the zone approach, the reality of daily use can be cumbersome. As a patient improves on therapy, his personal best may increase several times within a year. With each new personal best there must be a re-calculation to cutoff levels for each zone. The patient must constantly remember new cutoffs or else frequently refer to a complex table. This turns a simple instrument that has a simple maneuver for use into a cumbersome task in order to derive a meaningful result. There has now been developed an improved spirometer for in-home use. The spirometer overcomes drawbacks associated with the known spirometers. The improved spirometer is capable of giving a current lung expiratory peak flow rate which can be readily compared to a historical peak flow rate for the individual to alert him or her to when an asthma condition is worsening.

SUMMARY OF THE INVENTION

A hand-held spirometer for in-home use has an air flow channel with a terminus for the individual to blow into, a flow rate measuring chamber in communication with the air flow channel and a zone graph in operable association with the flow rate measuring chamber. The zone graph has a series of zones ranging from a danger zone to a fully normal zone. The user of the spirometer is able to immediately compare the individual's current expiratory peak flow rate with a previously determined normal or historical peak flow rate for that individual to determine whether an asthma condition is worsening.

DETAILED DESCRIPTION OF THE INVENTION

Figure 1:
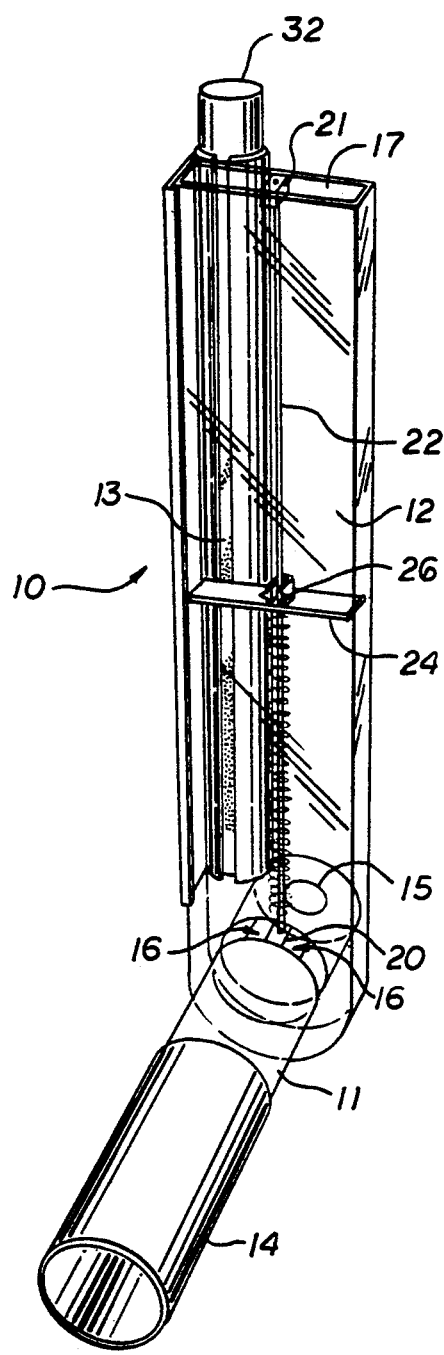
FIG. 1 is a perspective view of a spirometer of the invention.

The spirometer of this invention is described in the following paragraphs and with particular reference to the drawings. The components of the spirometer and its mode of use are described in detail.

With reference to FIGS. 1–4, there is shown a spirometer 10 of the invention. The spirometer 10 has as its essential components an air flow channel 11, a flow rate measuring chamber 12 and an adjustable zone graph 13. Construction and operation of the air flow channel and flow rate measuring chamber portions of the spirometer are based on the spirometer described in U.S. Pat. No. 4,944,306, Jul. 31, 1990, assigned to Healthscan, Inc., the disclosure of which is hereby incorporated herein.

The air flow channel 11 of the spirometer 10 is a cylindrical member with a mouthpiece 14 at one terminus and a reduced diameter exit orifice 1 at the other terminus. Intermediate the mouthpiece 14 and exit orifice 15 is the flow rate measuring chamber 12. The flow rate measuring chamber is an elongated translucent chamber which is mounted on the air flow channel 11 substantially perpendicular to the central axis of the channel and is in communication therewith through air passage 16 in a top wall of the channel. The flow rate measuring chamber 12 has an open top 17 and has a vertical slot 18 extending vertically down its backside. The slot accommodates an indicator as discussed in further detail below. Air which is blown into the mouthpiece of the spirometer flows through the air flow channel with a portion continuing through the channel and out the exit orifice 15 and another portion flowing into the flow rate measuring chamber and out its open top and vertical slot.

Positioned centrally within the flow rate measuring chamber 12 is a lower bridge 20 at the base of the chamber and an upper bridge 21 which is opposed oppositely at the top of the chamber. The bridges each have receptacles to anchor a rod 22 which lies along the chamber's central axis. At its base, the rod 22 has a horizontal bore through it which receives the lower end of an extension compression biased spring 23 and holds it in place. The upper end of the spring 23 is secured to the underside of a piston 24. As shown, an enlarged diameter hollow anchor 25 encompassing 20 the rod 22 extends down from the piston 24. The spring 23 is frictionally held to the anchor 25.

An indicator 26 is slidably secured in the vertical slot 18 and is operably associated with the piston 24. The indicator has a horizontal rod 27 extending from it and through the vertical slot 18. An enlarged head 28 at the end of the rod 27 and a compression spring 29 surrounding the rod 27 retain the indicator in place within the flow rate measuring chamber 12. The indicator rides up the chamber 12 with the piston 24 and remains at its highest point reached due to the compression spring 29. Positioned on the outer side of the chamber, most conveniently on its front wall, is a scale 30.

Figure 2:
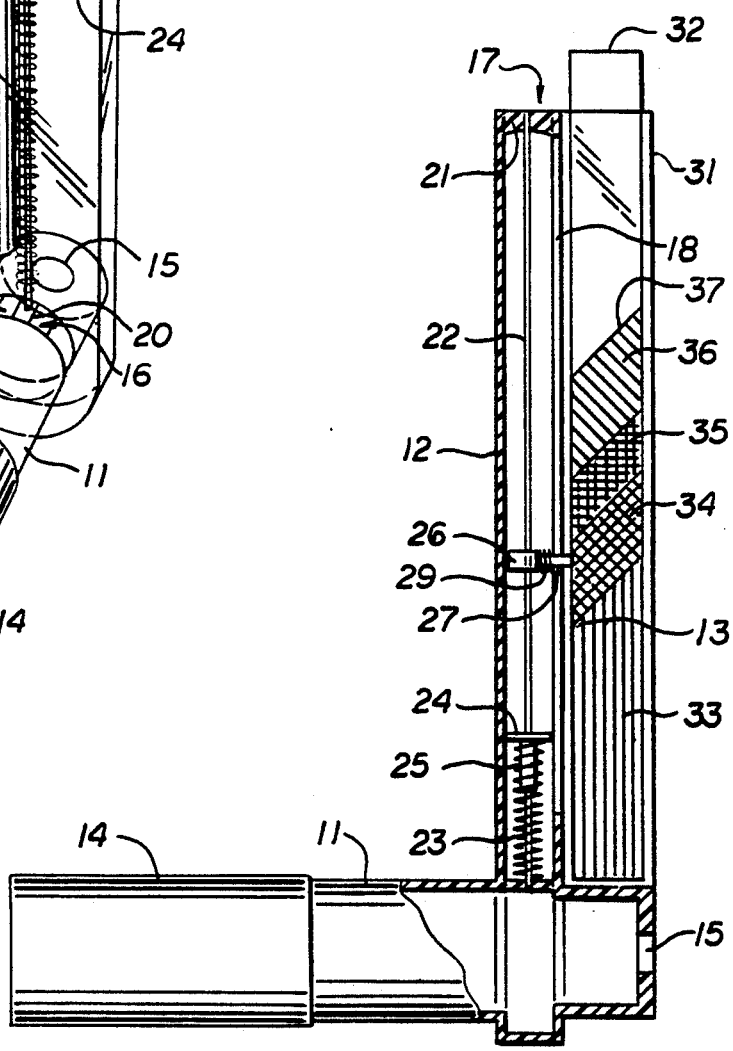
FIG. 2 is a side view partially in section of the spirometer of FIG. 1.
Figure 3:
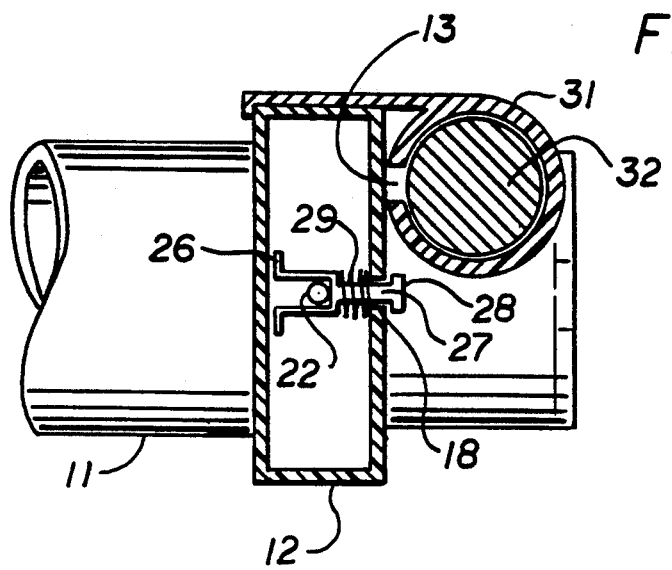
FIG. 3 is a top view partially in section of the spirometer of FIG. 1.
Figure 4:
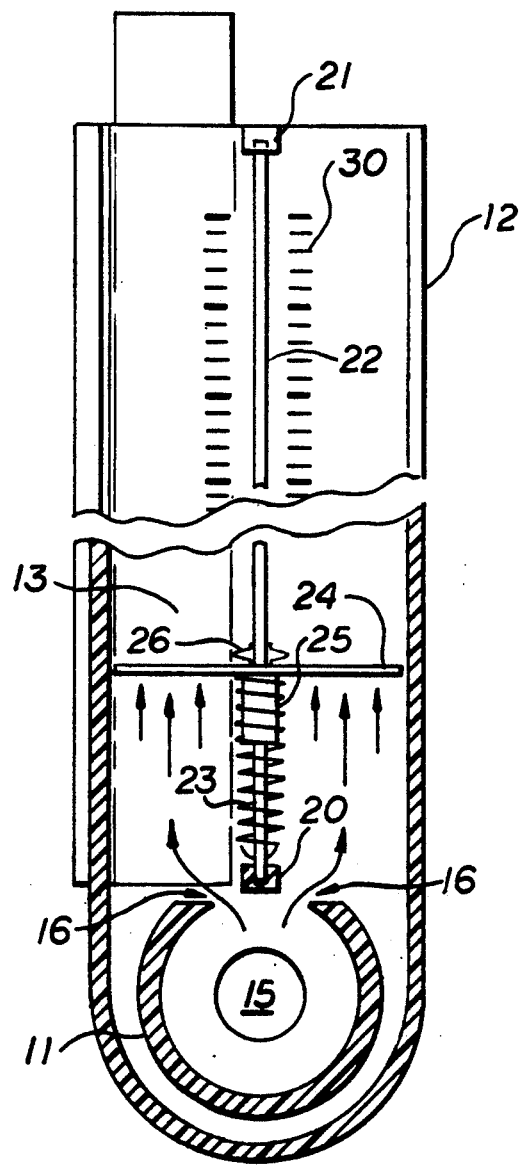
FIG. 4 is a front view partially in section of the spirometer of FIG. 1.

The adjustable zone graph 13 is in operable association with the flow rate measuring chamber 12. It is adjustable in that it is moveable relative to the indicator 26 used to measure the individual's current expiratory peak flow rate as above discussed. As best seen in FIGS. 2 and 3, the zone graph 13 is housed in a cylindrical-shaped holder 31. The holder 31 is mounted substantially perpendicularly on an outside wall of the air flow channel 11 and directly behind the flow rate measuring chamber 12. The zone graph is printed onto the face of a rod 32 and the rod 32 is rotatably positioned within the holder 31. As shown, the zone graph has four color zones ranging from a lowermost red danger zone 33 to an uppermost green fully normal zone 36. An orange zone 34 and a yellow zone 35 are intermediate the red and green zones. The particular zone boundary lines are determined in accordance with previously accepted procedures wherein the green zone represents 80% to 100% of a personal best, the yellow zone represents 65% to 80% of the personal best, the orange zone represents 50% to 65% of the personal best and the red zone represents 0% to 50% of the personal best. Other zone graphs based on a lesser or greater number of zones and different percentages of personal best can be used and are contemplated herein.

The rod 32 with the zone graph 13 is frictionally held within the holder 31. A top portion of the rod extends out the top of the holder 31 to provide a means whereby the rod with its zone graph can be manually rotated during use as further described below. The outside diameter of the rod and the inside diameter of the housing are such as to allow the rod to rotate under a manual force, yet remain stationary during periods of non-use.

In operation, the patient places his lips to the mouthpiece of the spirometer, then proceeds to blow into it. A portion of the air passing through the mouthpiece will move through the air passages 16 in the top wall of the air flow channel 11 and impinge on the lower surface of the piston 24 with a force. This force will cause the piston 24 to move against the force stored in the extension biased spring 23. Depending on the force, the piston will be moved up a certain distance within the chamber. The indicator 26 is forced to move up the flow rate measuring chamber to a peak, where it is held stationary by the compression spring 29. The piston 24 then returns to its resting position. The current expiratory flow rate is read on the scale 30 adjacent to the indicator 26. At the same time, the indicator 26 points to a zone on the zone graph 13. The indicator is then manually reset to the bottom of the chamber 13 by pushing down on the protruding enlarged head 28 and two more readings promptly taken. The highest of the three readings is taken as the current reading. The zone graph is twisted until the highest of the three readings is in alignment with the top boundary line 37 defining the green zone. 36. This represents the individual's current "personal best" reading. The zone graph is retained in position for comparison with future readings.

In subsequent days, use of the spirometer may give a reading which exceeds the previously recorded high on the zone graph. Each time a new high is reached on the graph, the user twists the zone graph rod until the indicator 26 is in alignment with the top boundary line defining the green zone. This represents the individual's historical peak flow rate. This allows future readings to be immediately visually translated into a current zone on the graph zone and which is in relationship to the past or historical personal best reading. For example, if the current flow rate falls into the intermediate yellow or orange zones, the individual will know that an asthma attack is imminent. This often occurs prior to the normal symptoms of shortness of breath, coughing and wheezing. This allows the individual to begin a previously prescribed self-medication plan.

It should be readily apparent that the zone graph is easily set to indicate the user's personal best. A subsequent use of the spirometer even weeks later gives a reading on the scale which falls into a zone on the zone graph. The zone graph may have to be reset as above discussed to indicate a new personal best. Most importantly, the comparison of the current reading in a zone will indicate to the individual how the current lung expiratory rate relates to the previously determined rate.

Figure 5:
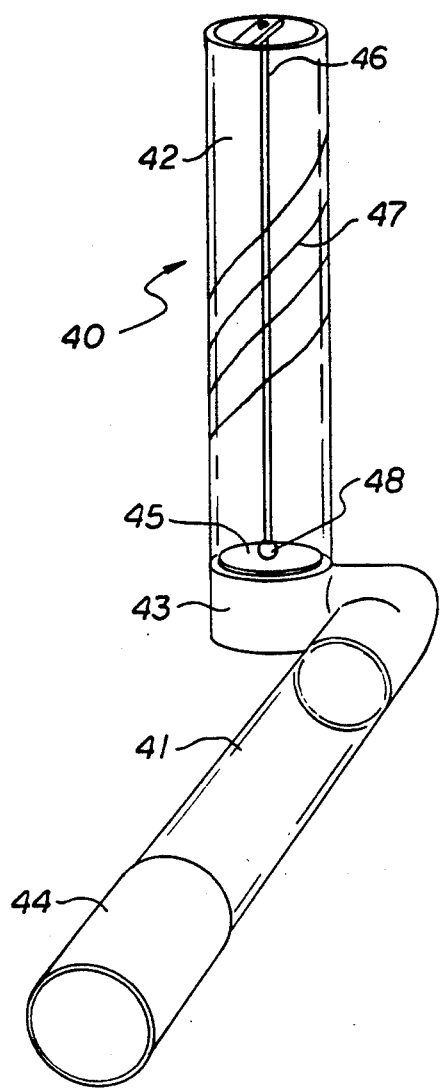
FIG. 5 is a perspective view of another embodiment of the spirometer of the invention.

FIG. 5 illustrates another embodiment of the invention. The spirometer 40 is designed to fold into a compact unit which can be more conveniently carried by an individual. The spirometer comprises an air flow channel 41 rotatably secured to a transparent flow rate measuring chamber 42. The channel 41 and chamber 42 are in communication at their point of attachment through a revolvable connecting member 43. A mouthpiece 44 is provided at one terminus of the airflow channel 41. The flow rate measuring chamber 42 has a slot on its backside to allow air to pass. A piston 45 mounted on a centrally disposed rectangular rod 46 within the flow rate measuring chamber is used to measure the individual's lung expiratory flow rate. The piston 45 is similar in construction and operation to the piston described with reference to FIGS. 1-4. The piston 45 moves according to the force of air blown into the mouthpiece by the individual. Some of the blown air exits the 15 spirometer through the slot on the backside of the chamber 42. An indicator dot 48 associated with the plunger records the individual's peak flow rate.

A zone graph 47 comprised of translucent color bands is positioned on the surface of the flow rate measuring chamber 42. The zone graph 47 is similar to the zone graph discussed above with reference to FIGS. 1-4. Operation of the spirometer 40 is also similar to the spirometer of FIGS. 1-4. The individual blows into the mouthpiece to cause the piston 45 to rise in the chamber. The piston is frictionally held in place. An indicator dot 48 on the front base of the piston 45 indicates the current zone. A new "personal best" is reached if the indicator dot rises above the top boundary line of the green zone. The chamber 42 is then rotated so that the top boundary line aligns with the indicator dot. In effect, the zones have now been reset to correspond to the new personal best flow rate. Subsequent uses of the spirometer in succeeding days will indicate current peak flow zones which are compared to the historical peak flow rate.

Figure 6:
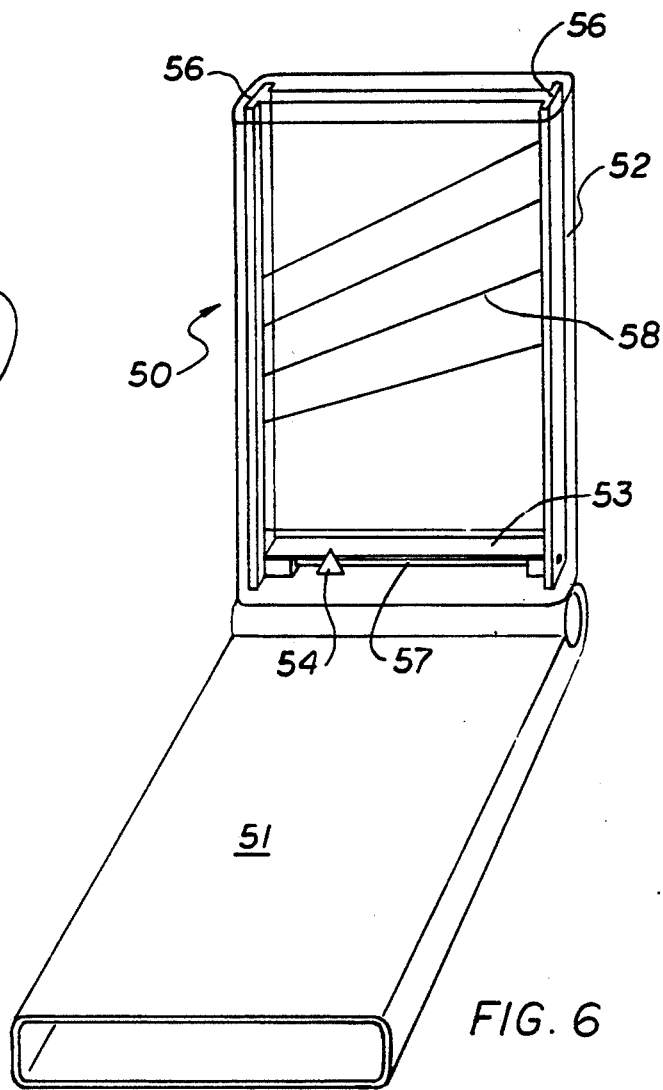
FIG. 6 is a perspective view of still another embodiment of the spirometer of the invention. 5
Figure 7:
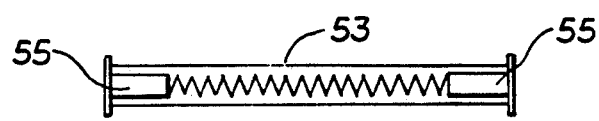
FIG. 7 is a top view of a piston used in the spirometer of FIG. 6.

FIGS. 6 and 7 illustrate still another embodiment of the invention. The spirometer 50 is a pocket sized instrument comprised of a hollow rectangular shaped air flow channel 51 and a hollow rectangular shaped flow rate measuring chamber 52 extending substantially perpendicular therefrom. The channel 51 and chamber 52 are hingeably attached to allow them to fold towards one another to form a flattened unit. The air flow channel 51 has a mouthpiece at one terminus to receive air blown into it by the individual. 15 The flow rate measuring chamber 52 has a slot in its backside through which air is expelled. The channel and chamber are in communication at their point of attachment such that blown air travels from the mouthpiece into the measuring chamber 52.

A piston 53 with an indicator 54 mounted in the spirometer 50 is 20 used to measure the individual's peak flow rate. The piston 53 as shown in FIG. 7 has spring loaded rivets 55 at each side to engage channels 56 extending along each side wall of the measuring chamber 52. As the piston rises in the chamber, the rivets slide along the channels until the piston stops. The piston is then held in 25 position by friction caused by the rivets 55 pressing against the walls of the channels 56. The indicator 54 is mounted on a rod 57 extending along the bottom of the piston 53. Ratchet teeth on the rod allow the indicator to move laterally in one direction.

A translucent zone graph 58 is provided on a face of the flow rate measuring chamber 52. In effect, the indicator 54 used to measure the individual's current expiratory peak flow rate is moveable relative to the zone graph. Use of the spirometer 50 is similar to the spirometer 10 described in detail above. Air blown into the air flow channel 51 continues through the hinged area into the flow rate measuring chamber 52. The air flow exerts a pressure to push the piston 53 upward. The piston rises in the measuring chamber proportional to the pressure exerted by the airflow. When it stops it remains at rest by friction means. The indicator 54 slides across the bottom of piston 53. The indicator 54 indicates in which zone the piston has stopped. If a new personal best peak flow rate is achieved, then the indicator is moved to the right to coincide with the top boundary line of the green zone.

Still other spirometers of various shapes are possible depending on the desires of the marketplace. For example, a compact flattened circular shaped spirometer comprises a air flow channel leading directly into a flow rate measuring chamber with a biased spring turbine vane and an associated color graph. Also a one piece elongated cylinder representing the air flow channel and flow rate measuring chamber is possible. Such a spirometer has a transparent zone graph on a transparent cylinder which revolves through the member's body. The indicator's position can be seen through the cylinder and operation of it is similar to that of the spirometer described above with the reference to FIG. 5. Still other embodiments are possible provided there is always an adjustable zone graph in operable association with a peak flow rate indicator which can be used to record a current peak flow rate and compare it to a historical peak flow rate.

While the invention has been described in detail with particular reference to the drawings, it should be understood that variations and modifications can be made to the spirometer. All changes of an obvious nature are considered within the scope of the appended 10 claims.

I claim:

1. A hand-held spirometer for in-home use by an individual disposed to respiratory disorders to measure the individual's current lung expiratory peak flow rate and compare said current peak flow rate to a previously determined historical peak flow rate, said spirometer comprising:
   (a) an air flow channel having a terminus adapted to receiving air blow by the individual;
   (b) a translucent flow rate measuring chamber in communication with the air flow channel with means to measure the individual's current expiratory peak flow rate, said means being a piston within the flow rate measuring chamber with an indicator operably associated therewith and wherein said piston is capable of movement in the flow rate measuring chamber in response to the air blow into the air flow channel; and
   (c) a holder having cylindrical-shaped wall mounted substantially perpendicularly on an outside wall of the air flow channel directly behind the flow rate measuring chamber, said holder having a rod rotatably positioned therewithin to frictionally engaged said cylindrical-shaped walls when manually rotated therein and a zone graph is on the rod so as to be in operable association with the flow rate measuring chamber, wherein the zone graph and the means to measure the current expiratory peak flow rate are movably adjustable with respect to one another, said zone graph having a series of zones to indicate the individual's personal state of lung function ranging from a danger zone to a fully normal zone wherein the individual's current expiratory peak flow rate is visually compared to the individual's historical expiratory peak flow rate to readily indicate the individual's relative personal state of lung function.

2. The spirometer of claim 1 wherein the zone graph comprises at least two color zones.

3. The spirometer of claim 2 wherein the zone comprises four color zones.

4. A hand-held spirometer for in-home use by an individual disposed to respiratory disorders to measure the individual's current lung expiratory peak flow rate and compare said current peak flow rate to a previously determined historical peak flow rate, said spirometer comprising:

(a) an air flow channel having a terminus adapted to receiving air blown by the individual;

(b) a flow rate measuring chamber in communication with the air flow channel with means operably associated therewith to measure the individual's current expiratory peak flow rate in response to the air blown into the air flow channel; and (c) a zone graph in operable association with the flow rate measuring chamber, said zone graph having a series of zones to indicate the individual's personal state of lung function ranging from a danger zone to a fully normal zone wherein the individual's current expiratory peak flow rate is visually compared to the individual's historical expiratory peak flow rate to readily indicate the individual's relative personal state of lung function, further wherein a position of the zone graph is adjustable in response to the means in the flow rate measuring chamber.

5. The spirometer of claim 4 wherein the zone graph is moveable relative to the indicator in the flow rate measuring chamber used to measure the individual's current expiratory peak flow rate.

6. The spirometer of claim 5 wherein the means in the flow rate measuring chamber to measure the individual's current expiratory peak flow rate is a piston with the indicator operably associated therewith, said piston capable of movement in the flow rate measuring chamber responsive to the air blown into the air flow channel.

7. The spirometer of claim 6 wherein the flow rate measuring chamber is translucent.

8. The spirometer of claim 7 wherein the zone graph is on a rod and said rod is rotatably positioned within a holder having cylindrical-shaped walls such that said rod frictionally engages said walls when manually rotated therein.

9. The spirometer of claim 8 wherein the cylindrical-shaped holder is mounted substantially perpendicularly on an outside wall of the air flow channel directly behind the flow rate measuring chamber.

10. The spirometer of claim 9 wherein the zone graph comprises four color zones.

11. A hand-held spirometer for in-home use by an individual disposed to respiratory disorders to measure the individual's current lung expiratory peak flow rate and compare said current peak flow rate to a previously determined historical peak flow rate, said spirometer comprising:

(a) an air flow channel having a terminus adapted to receiving air blow by the individual;

(b) a translucent flow rate measuring chamber in communication with the air flow channel with a piston having an indicator operably associated therewith, and further wherein said piston is capable of movement in said flow rate measuring chamber in response to the air blow into the air flow channel so as to measure the individual'current expiratory peak flow rate; and (c) a zone graph in operable association with the flow rate measuring chamber, said zone graph having a series of zones to indicate the individual's personal state of lung function ranging from a danger zone to a fully normal zone wherein the individual's current expiratory peak flow rate is visually compared to the individual's historical expiratory peak flow rate to readily indicate the individual's relative personal state of lung function, further wherein the zone graph is moveable relative to the indicator in the flow rate measuring chamber, said zone graph being positioned on a rod which is rotatably positioned within a holder having cylindrical-shaped walls so as to frictionally engage said walls when manually rotated therein.

12. The spirometer of claim 11 wherein the holder for the rod is mounted substantially perpendicularly on an outside wall of the air flow channel directly behind the flow rate measuring chamber.

13. The spirometer of claim 12 wherein the zone graph comprises at least two color zones.

14. The spirometer of claim 13 wherein the zone graph comprises four color zones.

* * * * *